US009257055B2

(12) United States Patent
Endo et al.

(10) Patent No.: US 9,257,055 B2
(45) Date of Patent: Feb. 9, 2016

(54) SMALL INTESTINE ENDOSCOPE TRAINING SIMULATOR

(75) Inventors: Yutaka Endo, Yokohama (JP); Hiroshi Uno, Tsuruoka (JP)

(73) Assignees: SHOWA UNIVERSITY, Tokyo (JP); KOKEN CO., LTD., Tokyo (JP)

( * ) Notice: Subject to any disclaimer, the term of this patent is extended or adjusted under 35 U.S.C. 154(b) by 165 days.

(21) Appl. No.: 13/394,427

(22) PCT Filed: Jul. 27, 2010

(86) PCT No.: PCT/JP2010/062595
§ 371 (c)(1),
(2), (4) Date: Mar. 6, 2012

(87) PCT Pub. No.: WO2011/027634
PCT Pub. Date: Mar. 10, 2011

(65) Prior Publication Data
US 2012/0164616 A1    Jun. 28, 2012

(30) Foreign Application Priority Data

Sep. 7, 2009   (JP) .................................. 2009-205849

(51) Int. Cl.
*G09B 23/30* (2006.01)
*G09B 23/28* (2006.01)
*A61B 1/00* (2006.01)

(52) U.S. Cl.
CPC .......... *G09B 23/285* (2013.01); *A61B 1/00057* (2013.01)

(58) Field of Classification Search
USPC ....................................................... 434/267
See application file for complete search history.

(56) References Cited

U.S. PATENT DOCUMENTS

| 2,345,489 | A | * | 3/1944 | Lord | 434/272 |
| 2,971,272 | A | * | 2/1961 | Barlow | 434/272 |
| 2,988,823 | A | * | 6/1961 | Rosenbloom | 434/272 |
| 3,376,659 | A | * | 4/1968 | Asin et al. | 434/272 |
| 4,087,933 | A | * | 5/1978 | Strongin | 446/183 |
| 4,938,696 | A | * | 7/1990 | Foster et al. | 434/267 |
| 5,518,407 | A | * | 5/1996 | Greenfield et al. | 434/272 |
| 5,947,743 | A | * | 9/1999 | Hasson | 434/262 |
| 8,403,676 | B2 | * | 3/2013 | Frassica et al. | 434/267 |

(Continued)

FOREIGN PATENT DOCUMENTS

| JP | 2004-49479 | 2/2004 |
| JP | 3679535 | 8/2005 |
| JP | 2008-197483 | 8/2008 |

*Primary Examiner* — Xuan Thai
*Assistant Examiner* — James Hull
(74) *Attorney, Agent, or Firm* — Hunton & Williams LLP

(57) ABSTRACT

It is possible to provide a small intestine endoscope training simulator (11) which allows to obtain a feeling similar to that of inserting an endoscope (38) into the small intestine (34) of the living body (30) and learn the actual operation of the endoscope (38). This training simulator (11) includes a plurality of longitudinal elastic members (32) for applying an elastic force to each of a plurality of portions of a simulated small intestine (13). One end portion sides of the plurality of longitudinal elastic members (32) are respectively attached to the first attachment portions (27) on the simulated small intestine (13) side. The other end portion sides of the plurality of longitudinal elastic members (32) are respectively attached to the second attachment portions (33, 57) on the case (12) side.

19 Claims, 9 Drawing Sheets

(56) References Cited

U.S. PATENT DOCUMENTS

| | | | |
|---|---|---|---|
| 8,556,635 B2* | 10/2013 | Toly | 434/272 |
| 2004/0199050 A1* | 10/2004 | Richardson | 600/116 |
| 2005/0008997 A1* | 1/2005 | Herman | 434/262 |
| 2005/0032028 A1* | 2/2005 | Chosack et al. | 434/262 |
| 2006/0275741 A1* | 12/2006 | Chewning et al. | 434/267 |
| 2008/0299529 A1* | 12/2008 | Schaller | 434/267 |
| 2009/0226868 A1* | 9/2009 | Frassica et al. | 434/272 |
| 2011/0269109 A2* | 11/2011 | Miyazaki | 434/267 |

* cited by examiner

SMALL INTESTINE ENDOSCOPE TRAINING SIMULATOR

CROSS REFERENCE TO RELATED APPLICATIONS

The present application is a national stage filing of PCT/JP2010/062595 filed Jul. 27, 2010 which claims priority to Japanese Application No. 2009-205849 filed Sep. 7, 2009. The disclosure of these priority applications are incorporated herein by reference in their entirety to the extent that it is consistent with this invention and application.

TECHNICAL FIELD

The present invention relates to a small intestine endoscope training simulator comprising a case having a space for a simulated abdominal cavity, and a simulated small intestine accommodated in the space for the simulated abdominal cavity.

BACKGROUND ART

The digestive tract of a living body extends from the mouth to the anus, with the esophagus, stomach, small intestine (divided into the duodenum, jejunum and ileum) and large intestine being connected in the order named between them. It is conventional practice for doctors to observe the inside of the digestive tract with an endoscope and perform a treatment such as hemostasis or excision of a polyp inside the digestive tract. However, targets for observation and treatment are limited to regions relatively close to the mouth or anus which is an insertion region of an endoscope. More specifically, when the doctor is to insert the endoscope through the mouth, a target range for observation or treatment includes up to the stomach and part of the duodenum. When the doctor is to insert the endoscope through the anus, a target range for observation or treatment includes up to the large intestine.

As conventional techniques for practicing the above observation and treatment, there are available an upper digestive tract endoscope training simulator simulating the esophagus, stomach and part of the duodenum of the living body (Japanese Patent Laid-Open No. 61-213877 "Endoscope Training Internal Organ/Digestive Tract Simulator") and a large intestine endoscope training simulator simulating organs from the anus to the large intestine of the living body (Japanese Patent Laid-Open No. 58-192523 "Large Intestine Endoscope Insertion Trainer"). The doctor can use these simulators to practice the operation of the endoscope.

Patent Reference 1: Japanese Patent Laid-Open No. 61-213877
Patent Reference 2: Japanese Patent Laid-Open No. 58-192523

Recently, by making improvements to conventional endoscopes, a balloon endoscope has been developed, which can be inserted into the small intestine (the jejunum and ileum, in particular) as the organ of the digestive tract, which is located farther from the upper digestive tract and large intestine, through the mouth or anus. This makes it possible to observe the inside of the small intestine and perform treatment such as hemostasis or excision of a polyp inside the small intestine. Accompanying this, demands have arisen for training simulators for practicing the insertion of an endoscope into the small intestine and operating it.

On the other hand, a capsule endoscope is on the market, which is swallowed through the mouth for the purpose of observing the small intestine. This capsule endoscope gives little pain to the patient at the time of use. This capsule endoscope, however, has disadvantages such as allowing only observation, incapability of treatment such as hemostasis or excision of a polyp or biopsy, and incapability of being used for a patient suspected to have obstruction or constriction of the intestinal tract. For this reason, capsule endoscopes have not replaced conventional endoscopes. These two types of endoscopes are thought to be selectively used in accordance with purposes in the future.

The small intestine is located deeper than the organs into which an endoscope has been inserted, and is itself a winding hollow organ. It is therefore very difficult to insert an endoscope into the small intestine and advance it to a target region even by using a balloon endoscope or the like which has recently been developed. For this reason, if an unskilled person operates the endoscope, he/she may not achieve an object because of incapability of observing a sufficiently large range of the small intestine. Furthermore, because of dangerous operation, he/she may damage the intestinal tract. Therefore, there has been a need for a training simulator for practicing the operation of inserting an endoscope into the small intestine.

DISCLOSURE OF INVENTION

The present invention is associated with a small intestine endoscope training simulator comprising a case having a space for a simulated abdominal cavity, and a simulated small intestine accommodated in the space for the simulated abdominal cavity, characterized by comprising a plurality of longitudinal elastic members for applying an elastic force to each of a plurality of portions of the simulated small intestine, wherein one end portion side of each of the longitudinal elastic members is attached to a corresponding one of a plurality of first attachment portions in a region including the plurality of portions and a vicinity thereof on the simulated small intestine side, and the other end portion side of each of the longitudinal elastic members is attached to a corresponding one of second attachment portions on the case side. The present invention can provide a training simulator which allows a doctor to learn to insert an endoscope into the small intestine and observe and treat the inside of the small intestine with the endoscope in a short period of time by properly selecting the positions of the first and second attachment portions and the like.

According to the first aspect of the present invention, the elastic force applied by each of the plurality of longitudinal elastic members, when the simulated small intestine stretches as the endoscope is inserted into the simulated small intestine, is preferably approximate to a restoring force on the small intestine by a mesentery of a living body toward an initial position. According to the second aspect of the present invention, the plurality of longitudinal elastic members are preferably gathered toward a substantially common portion from the one end portion sides of the longitudinal elastic members to the other end portion sides, and are preferably attached to the one or plurality of second attachment portions on the case side. According to the third aspect of the present invention, the other end portion sides of the plurality of longitudinal elastic members are preferably attached to the common second attachment portion on the case side. According to the fourth aspect of the present invention, the elastic force applied by the plurality of longitudinal elastic members to the simulated small intestine is preferably a tensile force acting substantially along a longitudinal direction of each of the plurality of longitudinal elastic members. According to the fifth aspect of the present invention, each of the plurality of longitudinal elastic members preferably comprises a rubber string and/or a coil spring. According to the sixth aspect of the present invention, each of the plurality of longitudinal elastic members preferably comprises a rubber string. According to the seventh aspect of the present invention, the number of the plurality of longitudinal elastic members preferably falls within a range of 3 to 10 (more preferably 4 to 8). According to the eighth aspect of the present invention, attachment intervals of the plurality of first attachment portions preferably fall within a range of 15 cm to 30 cm (more preferably 18 cm to 24 cm) in terms of lengths in an axial direction set when a virtual axis of the simulated small intestine is made linear.

According to the ninth aspect of the present invention, a load on the longitudinal elastic member at 100% stretching preferably falls within a range of 0.15 kg weight to 0.30 kg weight (more preferably 0.20 kg weight to 0.24 kg weight). According to the ninth aspect, it is possible to obtain a feeling very similar to that of actually inserting an endoscope into the small intestine of the living body. This further facilitates learning the actual operation of the endoscope.

According to the 10th aspect of the present invention, the small intestine endoscope training simulator can be configured to practice operation of inserting an endoscope into a small intestine from an anus through a large intestine. According to the 11th aspect of the present invention, the small intestine endoscope training simulator can be configured to practice operation of inserting an endoscope into a small intestine from a mouth through an esophagus and a stomach.

According to the 12th aspect of the present invention, the small intestine endoscope training simulator preferably comprises a simulated large intestine accommodated in a space for the simulated abdominal cavity, a sheet laid on an abdominal surface side of the simulated large intestine, and an opening provided in the sheet, wherein the simulated small intestine is preferably placed on an abdominal surface side of the sheet, and is connected to the simulated large intestine through the opening, and the sheet preferably substantially covers the simulated large intestine and portions of simulated small intestine which are closer to a back surface side than the opening. According to the 12th aspect, a portion of the simulated small intestine which is close to a connecting portion with the simulated large intestine is restricted movement thereof, and a portion of the simulated small intestine which is far from the connecting portion with the simulated large intestine can move relatively freely and smoothly. This makes it possible to obtain a feeling further similar to that of actually inserting an endoscope into the small intestine from the anus of the living body through the large intestine and to learn more practical operation of the endoscope.

According to the 13th aspect of the present invention, the plurality of first attachment portions preferably include portions closer to the abdominal surface side than the sheet and portions closer to the back surface side than the sheet, the longitudinal elastic member having the one end portion side attached to the portion closer to the abdominal surface side than the sheet preferably passes through the abdominal surface side rather than the sheet and extends to the second attachment portion, and the longitudinal elastic member having the one end portion side attached to the portion closer to the back surface side than the sheet preferably passes through the back surface side rather than the sheet and extends to the second attachment portion. According to the 13th aspect, even if the sheet is laid, it is possible to select a plurality of first attachment portions at substantially the same positions as those when no sheet is laid. In addition, it is substantially possible not to make the sheet from interfering with the movement of the longitudinal elastic members. This makes it possible to obtain a feeling further similar to that of actually inserting an endoscope into the small intestine from the anus of the living body through the large intestine, and hence allows to learn the further practical operation of the endoscope.

According to the 14th aspect of the present invention, the simulated small intestine is configured to be in contact with an inner surface of the simulated abdominal cavity throughout a substantially total length of the simulated small intestine in a longitudinal direction thereof, and the inner surface of the simulated abdominal cavity can have smoothness to allow the simulated small intestine pressed inwardly by an endoscope inserted into the simulated small intestine to move along the inner surface of the simulated abdominal cavity. According to the 14th aspect, no problem arises even if there is neither a simulated large intestine nor a sheet for reducing the unevenness caused by a simulated large intestine. It is therefore possible to implement, at a low cost, a small intestine endoscope training simulator for learning the operation of inserting an endoscope into the small intestine from the mouth of the living body through the esophagus and stomach.

According to the 15th aspect of the present invention, the case preferably comprises a case main body and a top sheet member which is attached to the case main body so as to be configured to seal and open the top opening formed in an upper surface of the case main body. According to the 16th aspect of the present invention, the case preferably comprises an opaque lower case member, a transparent upper case member detachably connected to the lower case member, and a top sheet member which is attached to the upper case member so as to be configured to seal and open the top opening formed in an upper surface of the upper case member. According to the 17th aspect of the present invention, the lower case member preferably comprises a shelf portion and rising wall portions for forming a space for the simulated abdominal cavity. According to the 15th to 17th aspects, it is possible to manufacture, at a low cost, a case which prevents a simulated living organ such as a simulated small intestine from accidentally gathering dust and the like by being exposed to the outside, and allows easy handling.

According to the 18th aspect of the present invention, the training simulator preferably comprises a mounting plate or mounting base for mounting the case thereon, and further comprising an engaging mechanism which selectively allows to mount the case on the mounting plate or mounting base in a substantially horizontal state and to mount the case on the mounting plate or mounting base in a substantially vertical state. In this case, the above engaging mechanism can comprise a plurality of engaging pins provided on one of the case and the mounting plate or mounting base and a plurality of engaging holes provided in the other of the case and the mounting plate or mounting base. According to the 18th aspect, it is possible to use, for the practice of the operation of an endoscope, the common small intestine endoscope training simulator both in a state similar to the state in which the living body lies on his/her back (that is, lies in a dorsal position) and in a state similar to the state in which the living body lies on his/her side (that is, lies in a side decubitus position). Therefore, it is possible to practice endoscope operation associated with substantially two kinds of body positions of the living body by using a single small intestine endoscope training simulator.

BEST MODE FOR CARRYING OUT THE INVENTION

Figure 1:
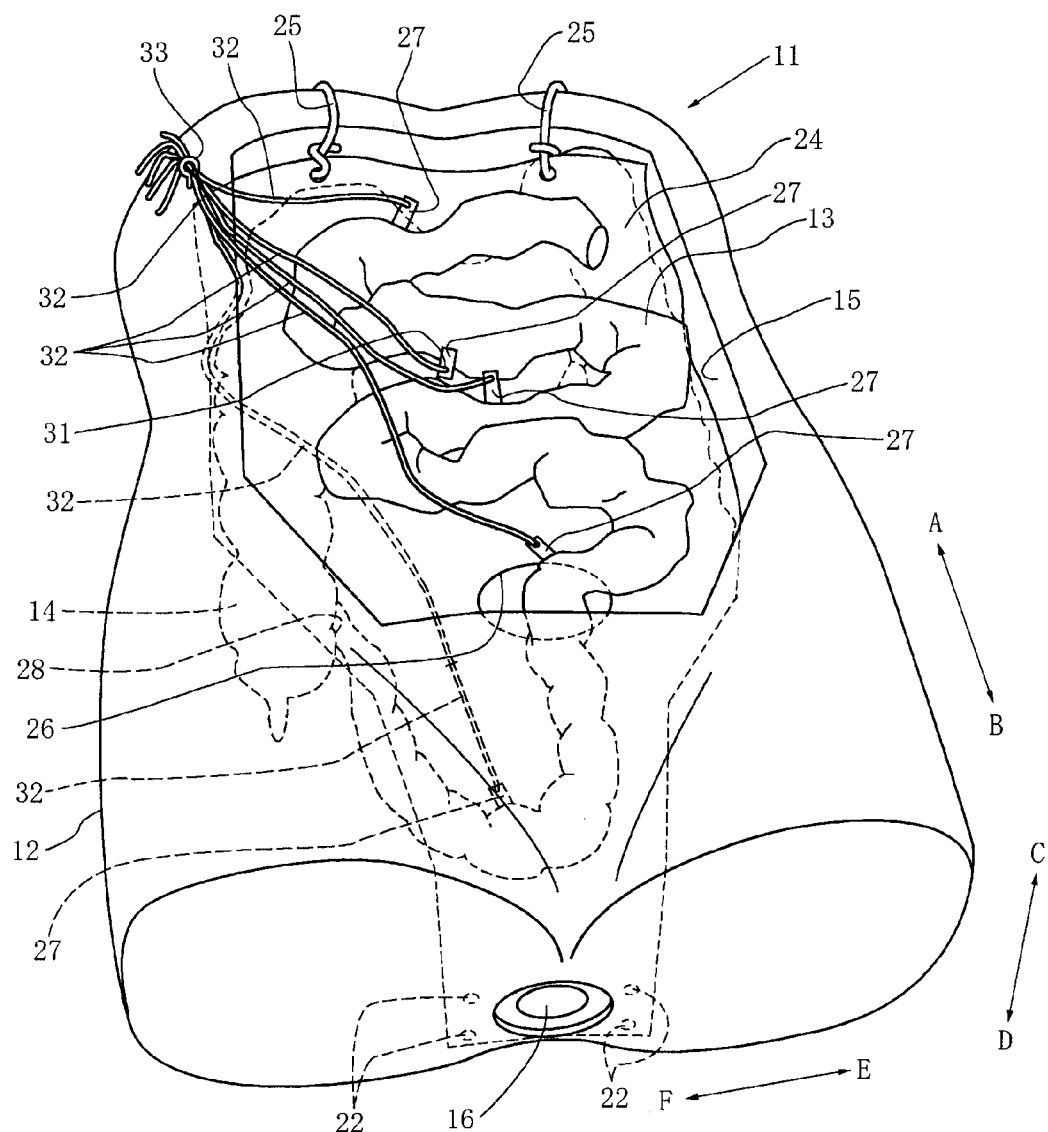
FIG. 1 is a perspective view of a small intestine endoscope training simulator according to the first embodiment to which the present invention is applied.

In the living body, the small intestine except for the duodenum adheres to the mesentery extending from the rear wall of the abdominal cavity. This mesentery is a membranous structure which is very flexible and stretchable. This allows the small intestine to move inside the abdominal cavity upon application of a force thereto.

As an endoscope (more specifically, the insertion tube portion of the endoscope) is inserted into the small intestine through the anus and large intestine or through the mouth, esophagus and stomach, the small intestine is pressed from the inside by the endoscope and stretched outward from the body. At this time, since the mesentery is extended, as the mesentery contracts to the initial state, the force that restores the stretched small intestine toward the center of the body acts on the small intestine. In practicing the operation of the endoscope, it is very important that such a force that restores the small intestine also acts on the simulated small intestine in the small intestine endoscope training simulator.

For this purpose, like the living body, the small intestine endoscope training simulator may have a simulated mesentery made of a highly flexible and stretchable material attached to the simulated small intestine. In practice, however, it is difficult to find a material which is rich in flexibility and stretchability like the mesentery of the living body and has durability high enough to pose no practical problem. Even if such a material is found, since a simulated mesentery is to be attached to a simulated small intestine throughout its total length, it is difficult to manufacture a small intestine endoscope training simulator. This makes it impossible to provide a small intestine endoscope training simulator at a practical price.

The present inventor has found that it is possible to make the user of the small intestine endoscope training simulator (to be referred to as the "training simulator" hereinafter) to have a feeling very similar to that of inserting the endoscope into the small intestine of the living body even by using a relatively simple structure attaching tags (in other words, attachment pieces made of cloth, a synthetic resin or the like) to the jejunum and ileum of the simulated small intestine at intervals of 15 cm to 30 cm, attaching one end portion side of longitudinal elastic members to the attachment pieces, and attaching the other end portion sides of the longitudinal elastic members to the housing of the training simulator (in other words, the case or case main body). The position at which such a longitudinal elastic member is attached to the case of the training simulator may be in the concave simulated abdominal cavity, of the case of the training simulator, in which the simulated small intestine is accommodated, simulating that the mesentery of the living body extends from the rear wall of the abdominal cavity. The present inventor, however, has also found that this position can be set to another position, for example, the outer surface of the case of the training simulator without posing any practical problem, as long as the direction in which the simulated small intestine is pulled almost coincides with that in the living body.

Assume that the elasticity of the longitudinal elastic member is expressed by the load generated when the longitudinal elastic member is stretched so as to increase the intervals between marks (that is, signs) attached to the longitudinal elastic member, which are 10 cm, to 20 cm (to be referred to as the "load at 100% stretching" hereinafter). In this case, the elasticity is preferably between 0.15 kg weight and 0.30 kg weight, more preferably between 0.20 kg weight and 0.24 kg weight. When, for example, the load at 100% stretching was 0.47 kg weight, the feeling of inserting the endoscope into the simulated small intestine was clearly different from that of inserting the endoscope into the small intestine of the living body. The above longitudinal elastic member may include an elastic cord or a coil spring made of a metal or soft synthetic resin.

The training simulator for the insertion of an endoscope into the small intestine from the anus through the large intestine inevitably includes a simulated large intestine, and the simulated small intestine needs to be connected to the large intestine. In the living body, a portion of the small intestine which is relatively close to the large intestine is folded in a zigzag pattern in the pelvic cavity. In simulating this, the training simulator also has part of the simulated small intestine folded and accommodated on the inferior limb side of the simulated abdominal cavity. In this state without any change, when an endoscope is inserted into the simulated small intestine through the simulated large intestine, the simulated small intestine greatly protrudes from the simulated abdominal cavity. This makes the training simulator greatly differ from the living body.

In order to prevent this, a flexible sheet is laid on the overall simulated abdominal cavity so as to cover the simulated large intestine, and part of the simulated small intestine is accommodated under the sheet. The remaining part of the simulated small intestine is extracted onto the sheet through a hole (in other words, an opening) formed in one portion of the sheet, and is placed on the sheet. In the living body, part of the small intestine which is located in the abdominal cavity other than pelvic cavity moves relatively largely. For this reason, in order to simulate this movement in this training simulator, the remaining part of the simulated small intestine is placed on the sheet as described above. In addition, the sheet allows the simulated small intestine to move without being interfered by the large intestine. Note however that since the longitudinal elastic member is attached to the simulated small intestine through the attachment pieces, this attachment imposes some limitation on the movement.

Using the longitudinal elastic members and the sheet in this manners makes both the sheet and the longitudinal elastic members greatly restrict the movement of part of the simulated small intestine which is located close to the simulated large intestine and in the pelvic cavity. In addition, only the longitudinal elastic member restricts the movement of part of the simulated small intestine which corresponds to part of the small intestine which is located outside the pelvic cavity in the living body, and hence the relatively free movement of the simulated small intestine is reproduced. In addition, the present inventor has also found that it is possible to adjust the degree of difficulty in inserting an endoscope by adjusting the amount of part of the simulated small intestine which is folded and accommodated under the flexible sheet.

It is also possible to use the training simulator for practicing the operation of an endoscope in accordance with a wide range of purposes by forming part of the simulated small intestine into a replaceable structure and replacing it with part of the simulated small intestine which is prepared separately. Such part of the simulated small intestine which is prepared separately may include various lesions or may be provided with a constriction region which makes it difficult to insert an endoscope. In this case, for example, one of the connecting portion of a non-replacement part of the simulated small intestine and the connecting portion of a replacement part can be provided with an outward or inward collar portion (in other words, an annular convex portion) while the other of the connecting portions can be provided with an inward or outward annular concave portion. This arrangement can connect the non-replacement portion of the simulated small intestine with the replacement portion by elastically deforming at least one of these connecting portions and fitting the annular concave portion on the annular convex portion.

The first to third embodiments of the present invention will be described in more detail below in items "1. First Embodiment", "2. Second Embodiment" and "3. Third Embodiment". Note however that the present invention is not limited to the first to third embodiments.

1. First Embodiment

Figure 2:
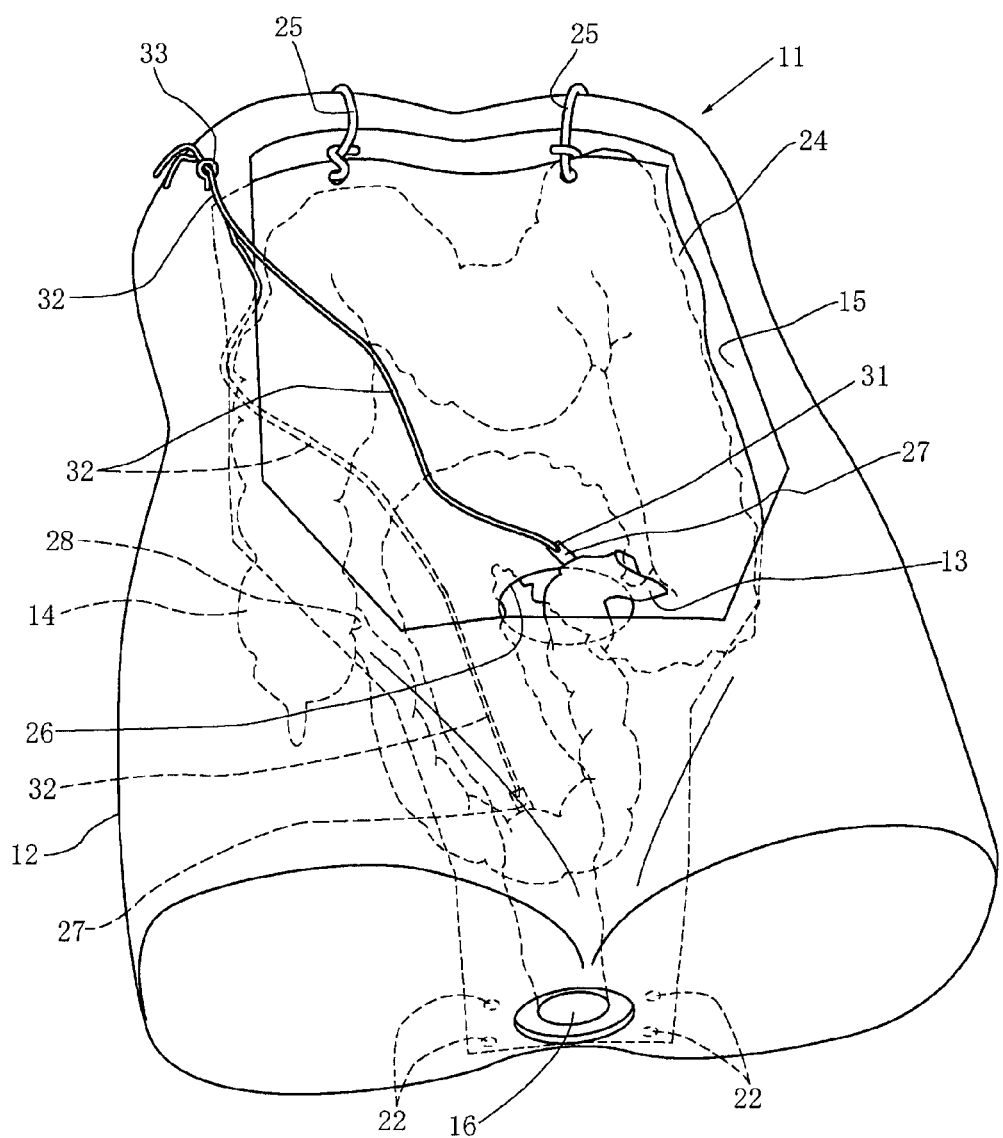
FIG. 2 is a perspective view of the small intestine endoscope training simulator shown in FIG. 1 from which most of the simulated small intestine is removed.
Figure 3:
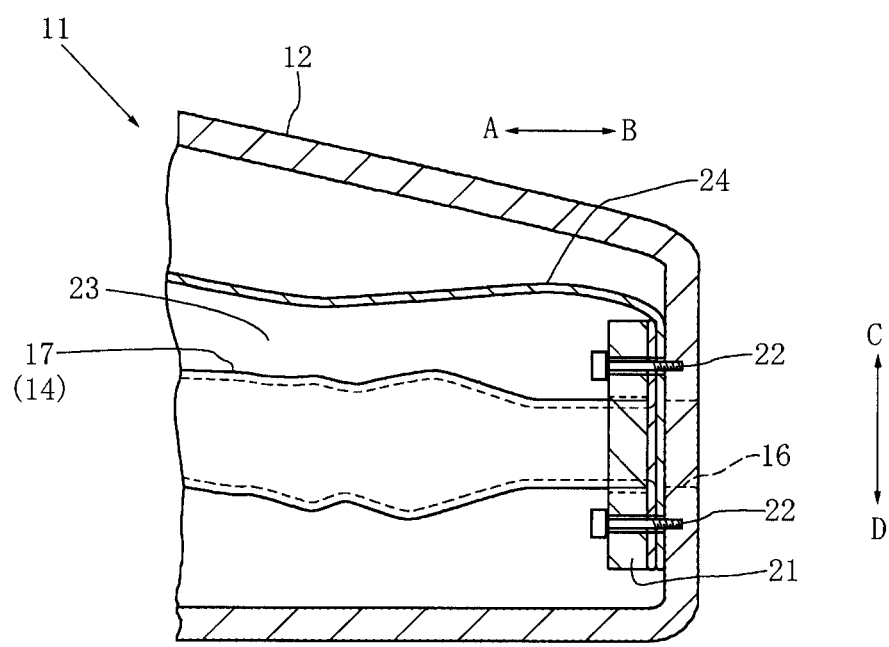
FIG. 3 is a longitudinal sectional view of a region including the anus and its vicinity of the small intestine endoscope training simulator shown in FIG. 1.

FIGS. 1 to 3 show a training simulator 11 according to the first embodiment which is used to practice the operation of inserting an endoscope into the small intestine from the anus through the large intestine. A case 12 of the training simulator 11 simulates the size and shape of the abdominal region of the human body (in other words, a region ranging from a region including the diaphragm and its vicinity to a region including the inguinal region and its vicinity). Referring to FIG. 1, arrows A and B respectively indicate the chest region side and inferior limb side of the training simulator 11 which respectively correspond to the chest region side and inferior limb side of the human body. In addition, arrows C and D respectively indicate the abdominal surface side and back surface side of the training simulator 11 which respectively correspond to the abdominal surface side and back surface side of the human body. Furthermore, arrows E and F respectively indicate the left side and right side of the training simulator 11 which respectively correspond to the left side and right side of the human body. The case 12 needs not simulate the softness of the human body. In the first embodiment, the case is made of a hard plastic material in consideration of the convenience of carrying the training simulator 11.

An abdominal surface side C of the case 12 is provided with a concave simulated abdominal cavity 15 simulating the abdominal cavity of the human body to accommodate a simulated small intestine 13 and a simulated large intestine 14. A simulated anus 16 is formed in a region including the center and its vicinity of an inferior limb side B of the case 12. An endoscope (more specifically, the insertion portion and endoscope insertion over tube of the endoscope) can be inserted through the simulated anus 16. As will be described later, the simulated anus 16 is connected to a simulated rectum 17 of the simulated large intestine 14.

As shown in FIGS. 1 to 3, the simulated abdominal cavity 15 of the case 12 allows the simulated large intestine 14 to be accommodated in a shape similar to that of the large intestine of the human body. In other words, a halfway portion of the ascending colon of the simulated large intestine 14 and a halfway portion of the descending colon of the simulated large intestine 14 are respectively bonded to plate-like bases. These bases are fixed to the bottom surface of the simulated abdominal cavity 15 with screws. The simulated large intestine 14 is made of silicone rubber to simulate the softness of the large intestine of the living body. The simulated large intestine 14 is molded into a tubular shape having annular folds like the large intestine of the living body, and has a thickness of about 0.7 mm to 1.0 mm. As shown in FIG. 3, the simulated rectum 17 of the simulated large intestine 14 is fixed to a region including the center and its vicinity of the inner surface side of the inferior limb side B of the case 12 with a pressing plate 21 and screws 22 so as to be coaxial with the simulated anus 16.

As shown in FIG. 3, a flexible, slippery vinyl chloride sheet 24 is laid on the simulated large intestine 14 (in other words, the abdominal surface side C) so as to cover the simulated large intestine 14 and form a simulated pelvic cavity 23 between the sheet 24 and the case 12. The vinyl chloride sheet 24 is fixed to the case 12 with strings 25 on the chest region side A. As shown in FIG. 3, on the inferior limb side B, the sheet 24 is fixed to a region including the center and its vicinity of the inner surface of the inferior limb side B of the case 12 with the pressing plate 21 and screws 22. Note that, as shown in FIG. 2, since the most part of the simulated small intestine 13 on the sheet 24 is removed from the training simulator 11, the structure under the sheet 24 is explicitly indicated by the broken lines and the like.

The simulated small intestine 13 is made of silicone rubber to simulate the softness of the small intestine of the living body. The simulated small intestine 13 is molded into a tubular shape having annular folds like the small intestine of the living body, and has a thickness of about 0.5 mm to 0.7 mm. Lesions and polyps are provided in the simulated small intestine 13. Using the training simulator 11 allows to learn the skill associated with observation of a lesion and treatments such as excision of a polyp.

As shown in FIG. 2, a portion of the simulated small intestine 13 which extends from a connecting portion 28 with the simulated large intestine 14 by a length of about 20 cm is placed under the sheet 24 while being folded or shaped in a loop. An opening 26 is formed in the sheet 24. The portion of the simulated small intestine 13 which extends from the connecting portion 28 with the simulated large intestine 14 by a length of about 20 cm passes through the opening 26. In addition, the portion of the simulated small intestine 13 which extends from the opening 26 can be placed on the sheet 24 properly in a meandering state. This placement can be freely implemented on the sheet 24.

In order to practice the operation of inserting an endoscope into the small intestine from the anus through the large intestine, it is sufficient for the simulated small intestine 13 to have a total length of about 1 m to 1.5 m. This is because, even if the total length of the simulated small intestine 13 is more than this length, the procedure for the operation of inserting the endoscope remains the same, and it is not necessary for the simulated small intestine to have a length more than this length.

As shown in FIG. 1, a total of five attachment pieces 27 are attached to the outer surface of the simulated small intestine 13 at proper intervals. The proper attachment intervals preferably fall within the range of 15 cm to 30 cm and more preferably the range of 18 cm to 24 cm in terms of lengths in the longitudinal direction of the simulated small intestine 13 (in other words, the axial direction set when the virtual axis of the simulated small intestine 13 is made linear). The attachment pieces 27 each have a hole (in other words, an opening) 31, to which one end portion of a rubber string 32 is attached. A rubber string attachment portion 33 to which the other ends of the rubber strings 32 can be attached is provided at a position on a right side F and chest region side A of the case 12. The other end portions of all the five rubber strings 32 respectively attached to the five attachment pieces 27 of the simulated small intestine 13 are attached to the rubber string attachment portion 33. More specifically, in order to perform such attachment, the rubber string attachment portion 33 is formed from an attachment having a passage hole through which the five rubber strings 32 are made to extend. The five rubber strings 33 are then made to extend through the passage hole and tied to the attachment portion 33 or knotted to prevent removal.

One of the attachment pieces 27 is attached to a portion of the simulated small intestine 13 which is folded or shaped in a loop under the sheet 24. The rubber string 32 attached to the attachment piece 27 extends under the sheet 24, rides onto the sheet 24 through the gap between a side end of the sheet 24 and the simulated abdominal cavity 15, and is attached to the rubber string attachment portion 33. The remaining four attachment pieces 27 are attached to portions of the simulated small intestine 13 which are arranged on the sheet 24. The rubber strings 32 attached to the four attachment pieces 27 extend on the sheet 24 and are attached to the rubber string attachment portion 33.

Figure 4:
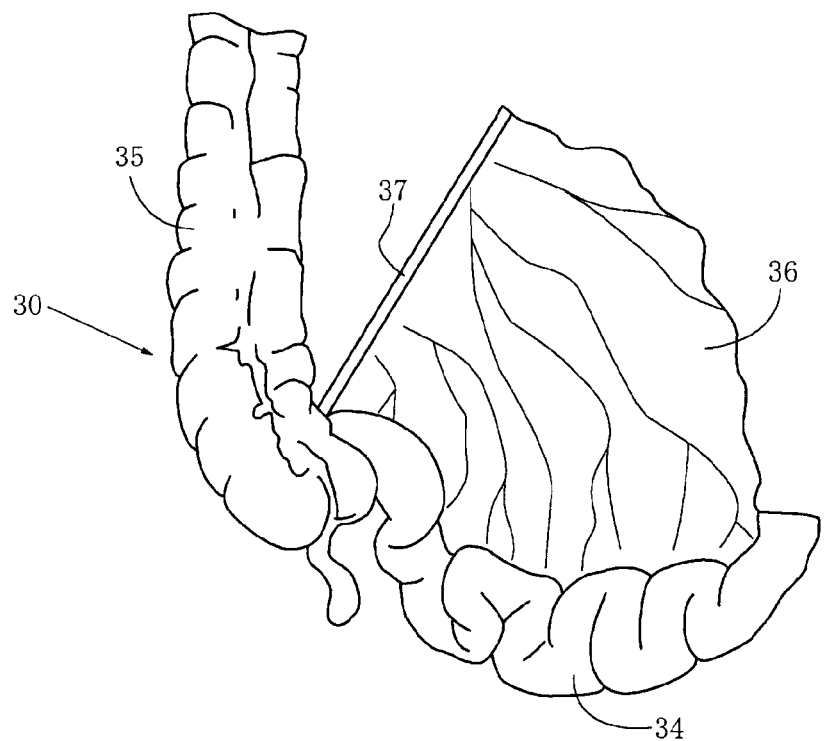
FIG. 4 is a front view of a region including the connecting portion and its vicinity between the small intestine and the large intestine in a state before the endoscope is inserted into the living body, and is the first reference view for explaining the first embodiment.
Figure 5:
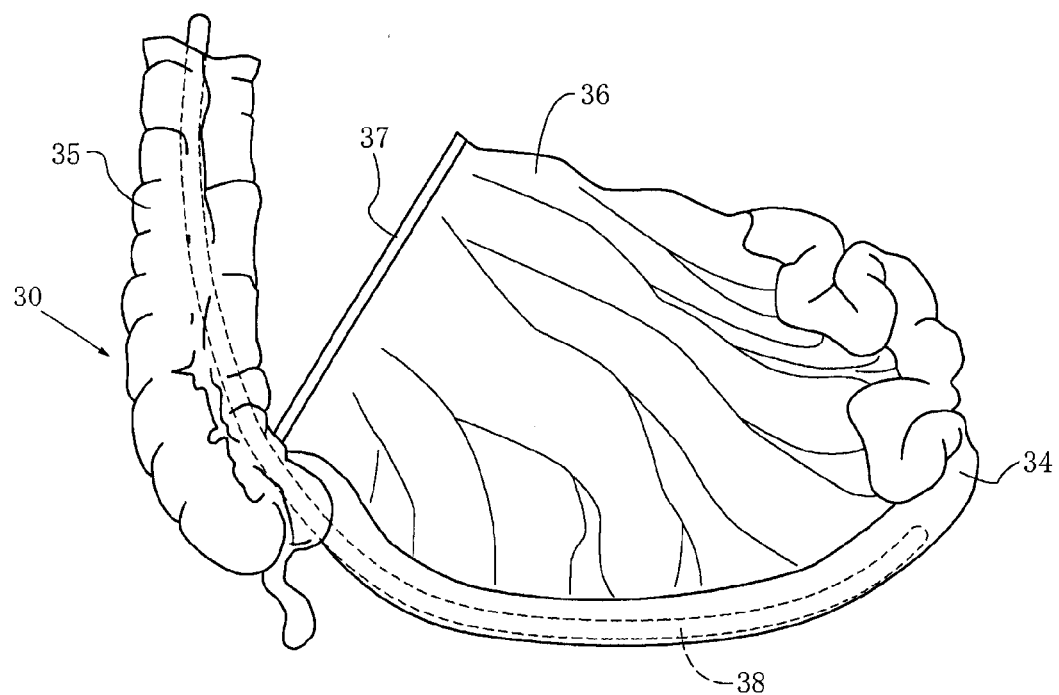
FIG. 5 is a front view of a region including the connecting portion and its vicinity between the small intestine and the large intestine in a state in which the endoscope is inserted into the small intestine through the anus and large intestine of the living body, and is the second reference view for explaining the first embodiment.

As shown in FIG. 4, in a living body 30, a portion of a small intestine 34 which is relatively close to a large intestine 35 is attached to a mesentery 36 extending from the rear wall of the abdominal cavity while being folded in a zigzag state. The mesentery 36 is attached to the rear wall of the abdominal cavity with an attachment portion 37 on the right side of the rear wall of the abdominal cavity (i.e., the right side viewed from the living body itself) and on the chest region side, and extends from the attachment portion 37 toward the small intestine 35. For this reason, as shown in FIG. 5, when the small intestine 34 extends as an endoscope 38 is inserted, the mesentery 36 applies a force on the small intestine 34 to pull it back toward the right chest region.

The rubber strings 32 simulate the function of the mesentery 36. Therefore, in the training simulator 11 as well, the rubber string attachment portion 33 is provided at a position on the right side F and chest region side A of the case 12 so as to make the force of pulling back the simulated small intestine 13 act in the same direction as the force generated by the mesentery 36. The rubber string 32 has a diameter of 3 mm, and the load at 100% stretching is 0.22 kg weight. The lengths of the respective rubber strings 32 match the distances from the rubber string attachment portion 33 to the attachment pieces 27 while the simulated small intestine 13 is placed on the sheet 24 so as to extend toward the chest region side A roughly in a zigzag state. More specifically, these lengths range from 10 cm to 50 cm.

2. Second Embodiment

The second embodiment is a training simulator 11 for practicing the operation of inserting an endoscope 38 into a small intestine 34 from the mouth through the esophagus and stomach. The same reference numerals as those used in the first embodiment denote portions in the second embodiment which correspond to those in the first embodiment described above. The simulated small intestine 13 in the training simulator 11 of the first embodiment described above simulates a portion (in other words, the ileum) of the small intestine 34 which is close to the large intestine 35. However, a simulated small intestine 13 of a training simulator 11 of the second embodiment simulates a portion (in other words, the jejunum) of the small intestine 34 which is close to the stomach and duodenum. When the endoscope 38 is inserted into a portion (in other words, the jejunum) of the small intestine 34 which is close to the stomach and duodenum, a mesentery 36 applies a force on the portion to slightly pull it to the upper left direction. For this reason, rubber strings 32 attached to attachment pieces 27 of the simulated small intestine 13 in the training simulator 11 of the second embodiment are attached at positions on a left side E and chest region side A of the case 12.

The second embodiment does not require the simulated large intestine 14, and hence does not require the sheet 24 covering the simulated large intestine 14. Note however that the inner surface of a simulated abdominal cavity 15 in which the simulated small intestine 13 is accommodated must not have any concave/convex portions which hinder the motion of the simulated small intestine 13 and must not be made of an un-slippery surface material.

3. Third Embodiment

FIGS. 6 to 10 show a training simulator 11 for practicing the operation of inserting an endoscope 38 into a small intestine 34 from the anus through a large intestine 35, as the third embodiment to which the present invention is applied. The arrangement and operation of the training simulator 11 according to the third embodiment basically differ in the following points from those of the training simulator 11 according to the first embodiment described above. The items described above in the first embodiment apply to the third embodiment unless inconsistency arises. The same reference numerals as those used in the first embodiment denote portions in the third embodiment which correspond to those in the first embodiment described above.

Figure 6:
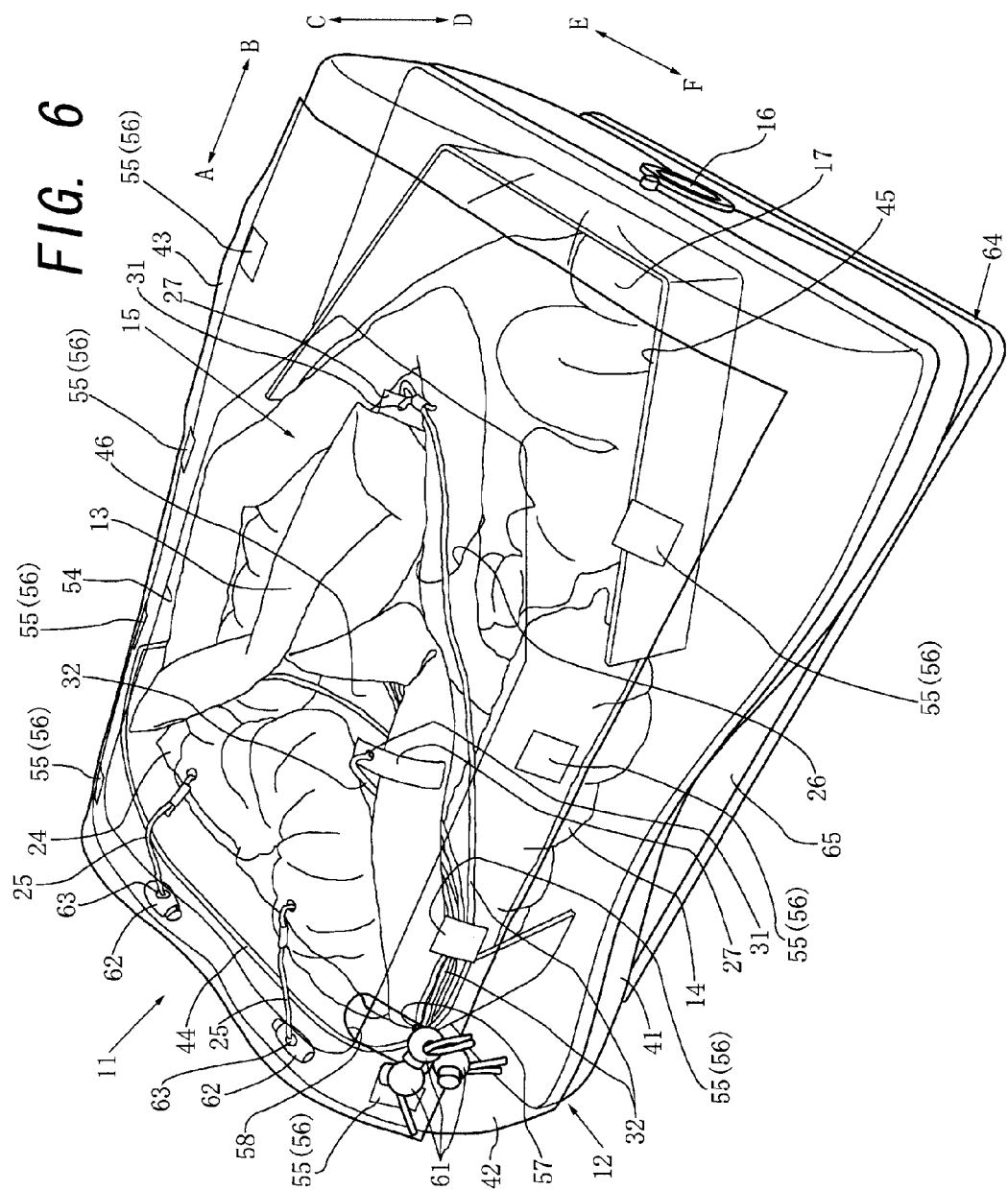
FIG. 6 is a perspective view of a small intestine endoscope training simulator with a mounting plate according to the third embodiment to which the present invention is applied.
Figure 7:
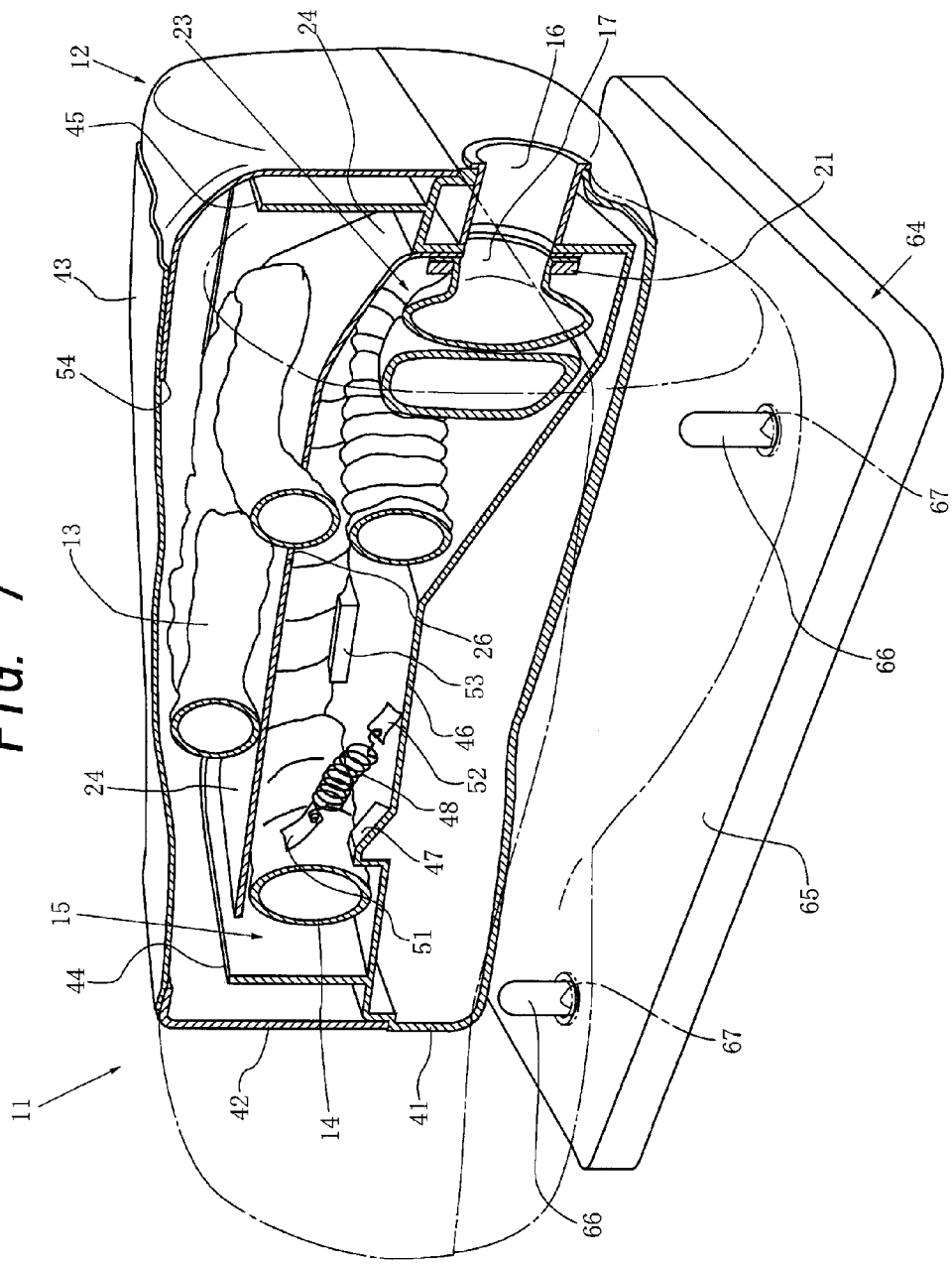
FIG. 7 is a longitudinal sectional view of the small intestine endoscope training simulator with the mounting plate shown in FIG. 6.

First of all, a case 12 in the third embodiment greatly differs from the case 12 in the first embodiment. The case 12 in the third embodiment includes a lower case member 41 which may be opaque, an upper case member 42 which may be transparent and a top sheet member 43 which may be transparent. When the upper case member 42 is fitted to the lower case member 41, the combinational structure of the lower case member 41 and the upper case member 42 is similar to the structure of the case 12 in the first embodiment, as shown in FIGS. 6 and 7. Note however that a wall portion of the lower case member 41, which protrudes from the upper surface of the lower case member 41 and is used for the formation of a simulated abdominal cavity, is divided into a rising wall portion 44 on a chest region side A and a rising wall portion 45 on an inferior limb side B.

The lower case member 41 includes a shelf portion 46. The shelf portion 46 extends obliquely downward to the inferior limb side B on the way. A cylindrical member with an outward flange for the formation of a simulated anus 16 is attached to the lower case member 41. A protruding portion 47 for holding the position of the simulated large intestine 14 or the like protrudes from the upper surface of the shelf portion 46. A coil spring (in other words, a longitudinal elastic member) 48 which elastically connects the simulated large intestine 14 to the shelf portion 46 is stretched on the upper side of the shelf portion 46. One end of the coil spring 48 is attached to the simulated large intestine 14 through an attachment piece 51. The other end of the coil spring 48 is attached to the shelf portion 46 through an attachment piece 52. Reference numeral 53 denotes a pair of left and right position holding members which hold the position of the simulated large intestine 14 by holding it from both the left and right sides of a proper portion. The position holding members 53 can be fixed to the shelf portion 46 with screws or the like. Part of the simulated large intestine 14 can be fastened to the upper surface of the position holding members 53 (in other words, an arcuated concave surface as part of a cylindrical surface) with an adhesive or the like.

An upper surface opening (in other words, a top opening) 54 which may have substantially the same shape as that of the upper surface opening of the simulated abdominal cavity 15 in the first embodiment is formed in the upper surface of the upper case member 42. The top sheet member 43 which can seal the upper surface opening 54 is attached to the upper surface of the upper case member 42. For this attachment, male or female surface fasteners (trademark: Magic Tape) 55 are provided at, for example, eight portions on the inner surface of the top sheet member 43. In addition, female or male surface fasteners (trademark: Magic Tape) 56 are provided at, for example, eight portions on the outer surface of the upper case member 42 in correspondence with the surface fasteners 55. Peeling off the top sheet member 43 from the upper case member 42 so as to release the mutual connection between the surface fasteners 55 and 56 can expose the simulated abdominal cavity 15 to the outside as in the case shown in FIG. 1 in the first embodiment.

In addition, the third embodiment differs from the first embodiment in the structure for attaching the rubber strings 32 to the case 12. That is, the outer end portions of the five rubber strings 32 extend outside the case 12 through a small opening 57 having a substantially circular shape or the like in the upper case member 42 and a large opening 58 having a substantially elliptic shape or the like in the top sheet member 43. Fasteners 61 having a substantially spherical, substantially columnar or the like which are commonly called "cord locks" are attached to the outer end portions of the rubber strings 32. In this case, one or a plurality of rubber strings 32 can be attached to one fastener 61. When the rubber strings 32 are pulled as the simulated small intestine 13 deforms, the fasteners 61 also serving as weights are pulled toward the opening 57 of the upper case member 42. However, the opening 57 is smaller than the fasteners 61, and hence there is no chance that the fasteners 61 will move to the inside of the upper case member 42 through the opening 57 from the outside of the upper case member 42 no matter how hard the fasteners 61 are pulled.

In the third embodiment, fasteners 62 similar to the fasteners 61 are used for strings 25 for attaching a sheet 24 to the case 12. The outer end portions of the strings 25 extend outside the upper case member 42 through openings 63 which are formed in the upper case member 42 and may have a shape similar to the openings 57. The fasteners 62 are then attached to the outer end portions.

In the third embodiment, the training simulator 11 includes a mounting plate 64 separately from the training simulator main body (in other words, the case 12). The mounting plate 64 includes a mounting plate main body 65 formed from a plate-like member made of wood or the like and having a substantially rectangular shape or the like and for example, a pair of positioning engaging pins 66 made of a metal or the like attached and fixed to the mounting plate main body 65 so as to protrude from one surface (more specifically, the upper surface) of the mounting plate main body 65. The positioning engaging pins 66 can be provided on the mounting plate main body 65 at positions offset to the left or right and substantially symmetrical about the direction from a chest region side A to an inferior limb side B. For example, a pair of positioning engaging holes 67 are provided at, for example, two corner portions of the lower surface of the case 12 (in other words, the lower case member 41) in correspondence with, for example, the pair of positioning engaging pins 66. In addition, for example, a pair of positioning engaging holes 68 are provided at, for example, two corner portions of the side surface of the case 12 (in other words, the lower case member 41) on a right side F in correspondence with the positioning engaging pins 66. For example, the positioning engaging holes 67 and 68 can be formed by partially embedding cylindrical members with outward flanges in the lower case member 41.

Figure 8:
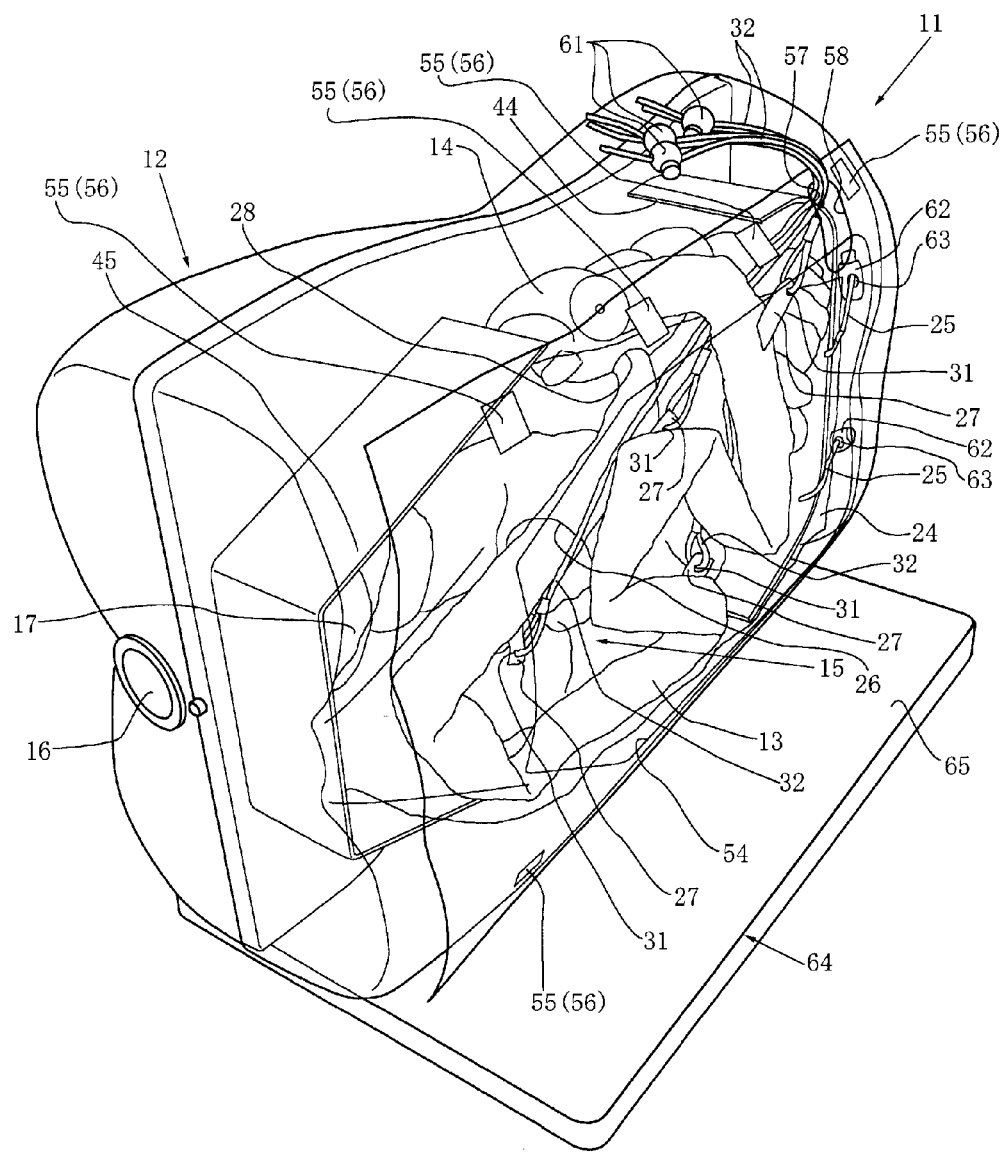
FIG. 8 is a perspective view of the small intestine endoscope training simulator with the mounting plate shown in FIG. 6 in another used state.
Figure 9:
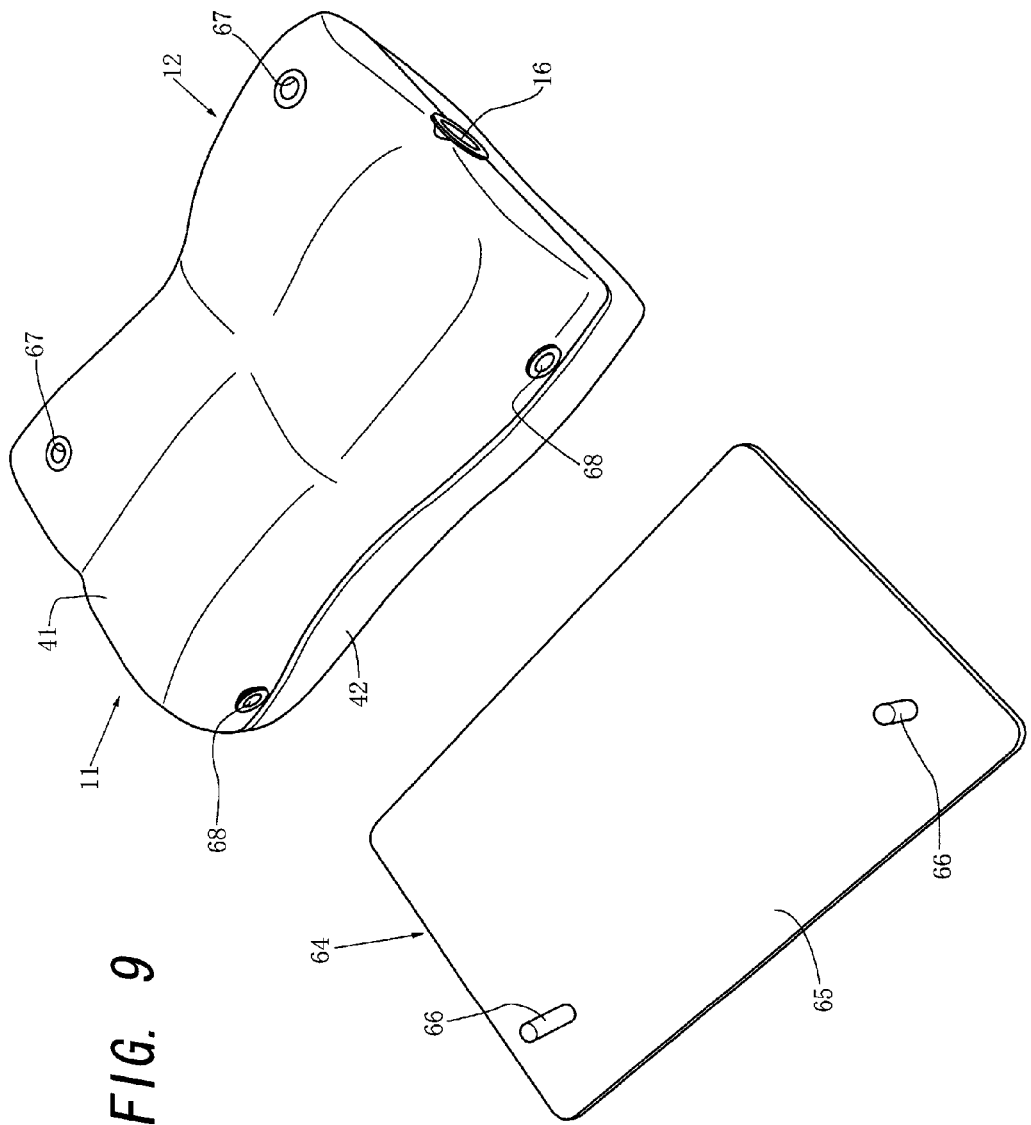
FIG. 9 is a perspective view of the small intestine endoscope training simulator with the mounting plate shown in FIG. 6 in a state in which the small intestine endoscope training simulator is separated from the mounting plate and is vertically inverted.

The training simulator 11 includes the mounting plate 64 having the above arrangement. Therefore, fitting, for example, the pair of positioning engaging pins 66 in, for example, the pair of positioning engaging holes 67 allows to use the training simulator 11 for the practice of the operation of the endoscope 38 while the training simulator 11 is set in a state similar to the state in which a living body 30 lies on his/her back (that is, lies in a dorsal position), as shown in FIGS. 6 and 7. In addition, fitting, for example, the pair of positioning engaging pins 66 in, for example, the pair of positioning engaging holes 68 allows to use the training simulator 11 for the practice of the operation of the endoscope 38 while the training simulator 11 is set in a state similar to the state in which the living body 30 lies on his/her side (that is, lies in a side decubitus position), as shown in FIG. 8.

Figure 10:
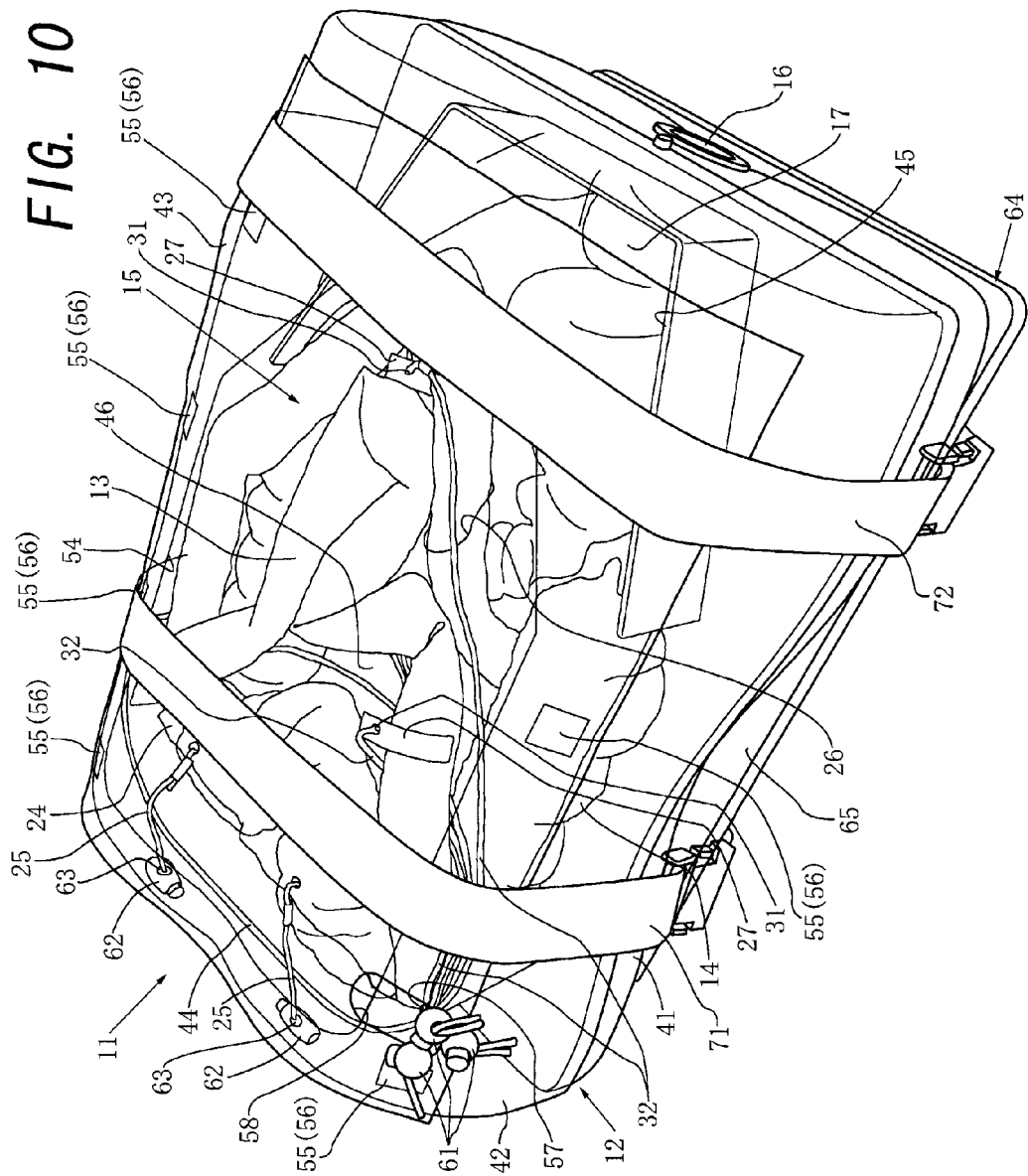
FIG. 10 is a perspective view of the small intestine endoscope training simulator with the mounting plate shown in FIG. 6 in an accommodated or transferred state.

FIG. 10 shows a state in which the training simulator 11 with the mounting plate shown in FIGS. 6 and 7 is accommodated in a proper place or transferred to a given place. In this case, as shown in FIG. 10, the training simulator 11 with the mounting plate shown in FIG. 6 includes a first fastening belt 71 wound and fastened around portions of the case 12 and the mounting plate 64 which are located on the chest region side A and a second fastening belt 72 wound and fastened around portions of the case 12 and the mounting plate 64 which are located on the inferior limb side B. Therefore, the training simulator 11 with the mounting plate shown in FIG. 10 is set in a state suitable for accommodation and transfer. In this case, the belts 71 and 72 may be attached to, for example, the lower surface of the mounting plate 64 in advance with screws or the like. In place of or in addition to the above screws, it is possible to provide belt loops (not shown) for the belts 71 and 72 on one or both of the mounting plate 64 and the case 12, as needed.

The first to third embodiments of the present invention have been described in detail above. However, the present invention is not limited to the first to third embodiments, and can be variously changed and modified within the spirit and scope of the invention defined by the appended claims.

For example, the training simulator 11 according to the first embodiment, which is designed for the practice of the operation of inserting the endoscope 38 into the small intestine 34 from the anus through the large intestine 35, is redesigned into the training simulator 11 for the practice of the operation of inserting the endoscope 38 into the small intestine 34 from the mouth through the esophagus and stomach in the second embodiment. The third embodiment described above can also be redesigned in the same manner. Performing such redesigning allows the training simulator 11 according to the third embodiment to be used for the practice of the operation of inserting the endoscope 38 into the small intestine 34 from the mouth through the esophagus and stomach.

In the third embodiment, the top opening 54 of the upper case member 42 is sealed by the top sheet member 43 which may be transparent. Top sheet members like the top sheet member 43 may be provided for the first and second embodiments. In this case, in the training simulators 11 according to the first and second embodiments, the top opening of the simulated abdominal cavity 15 is openably sealed by the top sheet member 43 which may be transparent as in the third embodiment described above.

The third embodiment includes the mounting plate 64 for allowing the case 12 of the training simulator 11 to be mounted thereon. However, the mounting plate 64 can be redesigned into a mounting base by providing leg portions for the mounting plate 64.

In the first and second embodiments, the outer end portion sides of all the longitudinal elastic members 32 are attached to the common rubber string attachment portion 33. However, the plurality of longitudinal elastic members 32 may be divided into two or more groups, and the outer end portion sides of the longitudinal elastic members 32 of the respective groups may be respectively attached to a plurality of rubber string attachment portions 33. In addition, the third embodiment may include a plurality of openings 57 as attachment portions, and the outer end portion sides of the plurality of longitudinal elastic members 32 may be selectively attached to the plurality of openings 57. Note however that in the present invention, it is preferable that the other end portion sides of all the longitudinal elastic members 32 each having one end portion side attached to a corresponding one of a plurality of portions of the small intestine 34 be gathered toward a substantially common portion, and then be collectively or not collectively attached to one or a plurality of portions on the case 12 side.

INDUSTRIAL APPLICABILITY

The present invention can be used for the manufacture or the like of a small intestine endoscope training simulator for allowing a doctor to learn to insert an endoscope into the small intestine and observe and treat the inside of the small intestine with the endoscope.

The invention claimed is:

1. A small intestine endoscope training simulator comprising:
 a case comprising a case main body that simulates the size and shape of an abdominal region of the human body having a space for a simulated abdominal cavity;
 a simulated large intestine accommodated in the space for said simulated abdominal cavity;
 a sheet laid over said simulated abdominal cavity;
 an opening provided in said sheet; and
 a simulated small intestine accommodated in the space for said simulated abdominal cavity, comprising:
  a plurality of longitudinal elastic members for applying an elastic force to a plurality of portions of said simulated small intestine, wherein a first end portion of each longitudinal elastic member is attached to a first attachment portion on the simulated small intestine, a second end portion of each of said longitudinal elastic members is tied to a second attachment portion on said case, each of said plurality of longitudinal elastic members comprises a rubber string, said plurality of rubber strings are substantially gathered together at the second end portions thereof,
 wherein a first portion of said simulated small intestine is positioned on top of said sheet outside of said simulated abdominal cavity and a second portion of the simulated small intestine is positioned below said sheet inside said simulated abdominal cavity such that the simulated small intestine passes through the opening in the sheet and is connected to said simulated large intestine under the sheet inside said simulated abdominal cavity, and wherein said sheet substantially covers said simulated large intestine and the second portion of the simulated small intestine in the simulated abdominal cavity.

2. The small intestine endoscope training simulator according to claim 1, wherein the elastic force applied by each of said plurality of longitudinal elastic members, when said simulated small intestine stretches as the endoscope is inserted into said simulated small intestine, is approximate to a restoring force on the small intestine by a mesentery of a living body toward an initial position.

3. The small intestine endoscope training simulator according to claim 1, wherein the elastic force applied by said plurality of longitudinal elastic members to said simulated small intestine is a tensile force acting substantially along a longitudinal direction of each of said plurality of longitudinal elastic members.

4. A small intestine endoscope training simulator according to claim 1, wherein a number of said plurality of longitudinal elastic members falls within a range of 3 to 10.

5. A small intestine endoscope training simulator according to claim 1, wherein a number of said plurality of longitudinal elastic members falls within a range of 4 to 8.

6. The small intestine endoscope training simulator according to claim 1, wherein the plurality of longitudinal elastic members are attached to the simulated small intestine in an attachment interval range of 15 cm to 30 cm in terms of length in an axial direction set when a virtual axis of said simulated small intestine is made linear.

7. The small intestine endoscope training simulator according to claim 1, wherein the plurality of longitudinal elastic members are attached to the simulated small intestine in an attachment interval range of 18 cm to 24 cm in terms of length in an axial direction set when a virtual axis of said simulated small intestine is made linear.

8. A small intestine endoscope training simulator according to claim 1, wherein a load on said longitudinal elastic member at 100% stretching falls within a range of 0.15 kg weight to 0.30 kg weight.

9. The small intestine endoscope training simulator according to claim 1, wherein a load on said longitudinal elastic member at 100% stretching falls within a range of 0.20 kg weight to 0.24 kg weight.

10. The small intestine endoscope training simulator according to claim 1, wherein said small intestine endoscope training simulator is configured to practice operation of inserting an endoscope into a small intestine from an anus through a large intestine.

11. The small intestine endoscope training simulator according to claim 1, wherein said small intestine endoscope training simulator is configured to practice operation of inserting an endoscope into a small intestine from a mouth through an esophagus and a stomach.

12. The small intestine endoscope training simulator according to claim 1, wherein said simulated small intestine is configured to be in contact with an inner surface of said simulated abdominal cavity throughout a substantially total length of said simulated small intestine in a longitudinal direction thereof, and the inner surface of said simulated abdominal cavity has smoothness to allow said simulated small intestine pressed inwardly by an endoscope inserted into said simulated small intestine to move along the inner surface of said simulated abdominal cavity.

13. The small intestine endoscope training simulator according to claim 1, wherein said case comprises a case main body and a top sheet member which is attached to the case main body so as to be configured to seal and open a top opening formed in an upper surface of the case main body.

14. The small intestine endoscope training simulator according to claim 1, wherein said case comprises an opaque lower case member, a transparent upper case member detachably connected to the lower case member, and a top sheet member which is attached to the upper case member so as to be configured to seal and open a top opening formed in an upper surface of the upper case member.

15. The small intestine endoscope training simulator according to claim 14, wherein the lower case member comprises a shelf portion and rising wall portions for forming a space for said simulated abdominal cavity.

16. The small intestine endoscope training simulator according to claim 1, comprising a mounting plate or mounting base for mounting said case thereon, and further comprising an engaging mechanism which selectively allows to mount said case on said mounting plate or mounting base in a substantially horizontal state and to mount said case on said mounting plate or mounting base in a substantially vertical state.

17. The small intestine endoscope training simulator according to claim 16, wherein said engaging mechanism comprises a plurality of engaging pins provided on one of said case and said mounting plate or mounting base and a plurality of engaging holes provided in the other of said case and said mounting plate or mounting base.

18. The small intestine endoscope training simulator according to claim 1, wherein the case is portable.

19. The small intestine endoscope training simulator according to claim 1, wherein the case is positioned on its side to simulate the human body lying in a side decubitus position.

* * * * *